US009254283B2

(12) United States Patent
Ikeda et al.

(10) Patent No.: US 9,254,283 B2
(45) Date of Patent: Feb. 9, 2016

(54) THERAPEUTIC AGENT FOR MIGRAINE

(75) Inventors: Junichi Ikeda, Shizuoka (JP); Shunji Ichikawa, Shizuoka (JP); Masako Kurokawa, Tokyo (JP); Tomoyuki Kanda, Shizuoka (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 541 days.

(21) Appl. No.: 13/055,005

(22) PCT Filed: Jul. 23, 2009

(86) PCT No.: PCT/JP2009/063151
§ 371 (c)(1),
(2), (4) Date: Mar. 16, 2011

(87) PCT Pub. No.: WO2010/010908
PCT Pub. Date: Jan. 28, 2010

(65) Prior Publication Data
US 2011/0183992 A1    Jul. 28, 2011

(30) Foreign Application Priority Data

Jul. 23, 2008  (JP) ................................. 2008-189610
Sep. 9, 2008   (JP) ................................. 2008-230657

(51) Int. Cl.
*A61K 31/535*   (2006.01)
*A01N 43/40*    (2006.01)
*A61K 31/44*    (2006.01)
*A61K 31/427*   (2006.01)
*A61K 31/519*   (2006.01)
*A61K 31/52*    (2006.01)
*A61K 45/06*    (2006.01)

(52) U.S. Cl.
CPC ............. *A61K 31/427* (2013.01); *A61K 31/519* (2013.01); *A61K 31/52* (2013.01); *A61K 45/06* (2013.01)

(58) Field of Classification Search
USPC ...................................................... 514/236.8
See application file for complete search history.

(56) References Cited

U.S. PATENT DOCUMENTS

| 6,222,035 | B1 | 4/2001 | Tsumuki et al. |
| 6,545,000 | B1 | 4/2003 | Shimada et al. |
| 7,141,575 | B2 | 11/2006 | Gillespie et al. |
| 7,230,102 | B2 | 6/2007 | Giorgio et al. |
| 7,384,949 | B2 | 6/2008 | Gillespie et al. |
| 7,528,252 | B2 | 5/2009 | Giorgio et al. |
| 7,718,808 | B2 * | 5/2010 | Nakajima et al. ............. 548/195 |
| 7,763,625 | B2 | 7/2010 | Takeuchi et al. |
| 7,880,013 | B2 | 2/2011 | Nakajima et al. |
| 7,910,613 | B2 | 3/2011 | Larsen et al. |
| 2002/0099061 | A1 | 7/2002 | Neustadt et al. |
| 2004/0097526 | A1 | 5/2004 | Gillespie et al. |
| 2006/0258721 | A1 * | 11/2006 | Maddaford et al. .......... 514/365 |
| 2007/0173505 | A1 | 7/2007 | Peng et al. |
| 2010/0152162 | A1 | 6/2010 | Uesaka et al. |
| 2011/0105465 | A1 | 5/2011 | Ouchi et al. |

FOREIGN PATENT DOCUMENTS

| EP | 2 308 509 A1 | 4/2011 |
| WO | 01/92264 | 12/2001 |
| WO | 2004-092173 A2 | 10/2004 |
| WO | WO 2005063743 A1 * | 7/2005 |

OTHER PUBLICATIONS

Blau, et al., "The site of pain origin during migraine attacks", Cephalalgia, vol. 1 (1981) 143-47.
Brown, et al., "Migraine precipitated by adenosine", Med. J. Aust, vol. 162 (1995) 389-91.
Ferrari, "Sumatriptan in the treatment of migraine", Neurology, vol. 43, Suppl 3 (1993) S43-47.
Ferré, et al., "Adenosine A2A receptors in ventral striatum, hypothalamus and nociceptive circuitry: Implications for drug addition, sleep and pain", Progress in Neurobiology, vol. 83 (2007) 332-47.
Fredholm, et al., "Actions of Caffeine in the Brain with Special Reference to Factors That Contribute to Its Widespread Use", Pharmacological Reviews, vol. 51, No. 1 (1999) 83-133.
Goadsby, et al., "Adenosine A1 receptor agonists inhibit trigeminovascular nociceptive transmission", Brain, vol. 125 (2002) 1392-1401.
Graham, et al., "Mechanism of Migraine Headache and Action of Ergotamine Tartrate", Arch. Neurol. Psychiatr., vol. 39 (1938) 737-63.
Guieu, et al., "Adenosine and Migraine", Le Journal Canadien Des Sciences Neurologiques, vol. 25, No. 1 (1998) 55-8.
Hadjikhani et al., "Mechanisms of migraine aura revealed by functional MRI in human visual cortex", PNAS, vol. 98, No. 8 (2001) 4687-92.
Hohoff, et al., "An adenosine A2A receptor gene haplotype is associated with migraine with aura", Cephalalgia, vol. 27 (2007) 177-81.
Humphrey, et al., "Serotonin and Migraine", Ann. NY Acad. Sci., vol. 600 (1990) 587-600.
Jacobson, et al., "Adenosine receptors as therapeutic targets", Nature Reviews, vol. 5 (2006) 247-64.
Kruuse, et al., "Dipyridamole may induce migraine in patients with migraine without aura", Cephalalgia, vol. 26 (2006) 925-33.

(Continued)

*Primary Examiner* — Layla Soroush
(74) *Attorney, Agent, or Firm* — Fitzpatrick, Cella, Harper & Scinto

(57) ABSTRACT

Provided are therapeutic and/or preventive agents for migraine which comprise, as an active ingredient, a compound having a selective adenosine $A_{2A}$ receptor antagonistic activity or a pharmaceutically acceptable salt thereof; therapeutic and/or preventive agents for migraine which comprise, as an active ingredient, a compound having a selective adenosine $A_{2A}$ receptor antagonistic activity, which has an affinity for the adenosine $A_{2A}$ receptor 10 times or higher than that for the adenosine $A_1$ receptor, or a pharmaceutically acceptable salt thereof; and the like.

1 Claim, No Drawings

(56) References Cited

OTHER PUBLICATIONS

Meno, et al., "Effect of adenosine receptor blockade on pial arteriolar dilation during sciatic nerve stimulation", Am J Physiol Heart Circ Physiol, vol. 281 (2001) H2018-27.

Neustadt, et al., "Potent, selective, and orally active adenosine A2A receptor antagonists: Arylpiperazine derivatives of pyrazolo[4,3-e]-1,2,4-triazolo[1,5-c]pyrimidines", Bioorganic & Medicinal Chemistry Letters, vol. 17, (2007) 1376-80.

Ngai, et al., "Receptor subtypes mediating adenosine-induced dilation of cerebral arterioles", Am J Physiol Heart Circ Physiol, vol. 280 (2001) H2329-35.

Nishizaki, "ATP- and Adenosine-Mediated Signaling in the Central Nervous System: Adenosine Stimulates Glutamate Release From Astrocytes via A2A Adenosine Receptors", J Pharmacol Sci, vol. 94 (2004) 100-2.

Nonaka, et al., "KF17837 ((E)-8-(3,4-dimethoxystyryl)-1,3-dipropyl-7-methylxanthine), a potent and selective adenosine A2 receptor antagonist", European Journal of Pharmacology, vol. 267, No. 3 (1994) 335-41.

O'Regan, "Adenosine and the regulation of cerebral blood flow", Neurological Research, vol. 27 (2005) 175-81.

Ramadan, et al., "New and future migraine therapy", Pharmacology & Therapeutics, vol. 112 (2006) 199-212.

Reichl, et al., "Inhibition of Neurosympathetic Cerebroarterial Constriction by Clonidine in Cats", European Journal of Pharmacology, vol. 68 (1980) 349-57.

Sawynok, "Pharmacological Rationale for the Clinical Use of Caffeine", Drugs, vol. 49, No. 1 (1995) 37-50.

Shin, et al., "Implication of adenosine A2A receptors in hypotension-induced vasodilation and cerebral blood flow autoregulation in rat pial arteries", Life Sciences, vol. 67 (2000) 1435-45.

Silberstein, "Migraine", The Lancet, vol. 363 (2004) 381-91.

Takano, et al., "Cortical spreading depression causes and coincides with tissue hypoxia", Nature Neuroscience, vol. 10, No. 6 (2007) 754-62.

Ward, et al., "The analgesic effects of caffeine in headache", Pain, vol. 44 (1991) 151-55.

Ayaka, et al., "Suppression of Cortical Spreading Depression in Migraine Prophylaxis", Annals Neurol., vol. 59, No. 4 (2006) 652-61.

Harrison's Principles of Internal Medicine, 15th ed., vol. 1 (2001) 78.

\* cited by examiner

THERAPEUTIC AGENT FOR MIGRAINE

TECHNICAL FIELD

The present invention relates to therapeutic and/or preventive agents for migraine.

BACKGROUND ART

Migraine is a paroxysmal headache that lasts 4 to 72 hours, accompanied by nausea, vomiting, sensitivity to light, sensitivity to sound, or the like [*The Merck Manual, Seventeenth Edition*, Chapter 168; *Therapeutic Guideline of The Japanese Society of Neurology; International Classification of Headache Disorders-II: ICHD-II*, 2004]. Vasodilation in the extra- and/or intra-cranial vessels including the superficial temporal artery has been proposed as one of the pathophysiology of migraine and its pathogenesis [*Arch. Neurol. Psychiatr.*, Vol. 39, p. 737-763 (1938); *Cephalagia*, Vol. 1, p. 143-147 (1981); *Internal medicine*, Vol. 81, p. 601-609 (1998); *Internal Medicine*, Vol. 81, p. 639 (1998)]. It has also been known that ergot alkaloid and sumatriptan, hydrophilic agonists of serotonin receptor 5-$HT_1$ (5-hydroxytryptamine 1), that do not cross the blood-brain barrier are effective for the treatment of migraine, because these agonists act on the serotonin receptor 5-$HT_1$ in the cerebral vascular smooth muscle to constrict the dilated blood vessels [*Ann. N.Y. Acad. Sci.*, Vol. 600, p. 587-600 (1990); *Neurology*, Vol. 43, p. S43-S47 (1993)].

It is thus believed that migraine can be treated by suppressing vasodilation in the extra- and/or intra-cranial vessels. Concerning the cause of migraine onset, there have also been reports presenting theories based on neurogenic inflammation around the trigeminal nerve and cerebral blood vessel, or around the dura mater blood vessel, or based on activation of the central nerve such as in cortical spreading depression [*Lancet*, Vol. 363, p. 381-391 (2004)].

There are further reports concerning migraine (see Non-Patent Documents 1 to 3).

Some of the examples of therapeutic agents for migraine currently in use in the clinic include non-steroidal antiphlogistic analgetics such as triptans (for example, sumatriptan), and ibuprophens. As for the preventive agents, for example, antiepileptic agents such as topiramate, and calcium antagonist agents such as flunarizine are currently used in the clinic.

It is known that the adenosine concentration in the blood plasma of migraine patients an hour after a migraine attack increases by an average of 68% from that during the normal period, and that the activation of the adenosine $A_2$ receptor by adenosine suppresses the serotonin uptake by platelets in a manner that depends on adenosine concentration, and causes vasodilation as a result of a rapid serotonin release [*Can. J, Neurol. Sci.*, Vol. 2, p. 55-58 (1998)]. Further, intravenous administration of an adenosine enhancer to a migraine patient is known to induce a migraine attack [*Med. J. Aust.*, Vol. 162, p. 389-390 (1995)]. It is also known that adenosine possesses a strong vasodilating action, and that the adenosine $A_{2A}$ receptor and the adenosine $A_{2B}$ receptor are involved in vasodilation during migraine and in adenosine-induced vasodilation [*Am. J. Physiol. Heart Circ. Physiol.*, Vol. 280, p. 2329-2335 (2001)]. It is thus believed that migraine can be treated by suppressing adenosine-induced vasodilation.

Caffeine, which has a non-selective adenosine antagonistic activity, is known to relieve migraine; however, caffeine has side-effects, namely, psychiatrical dependence, and causes caffeine withdrawal headache [see *Pain*, 1991, Vol. 44, p. 151-155; *Drugs*, 1995, Vol. 49, p. 37-50]. Further, xanthine derivatives are known to be useful as therapeutic drugs for migraine (see Patent Document 1).

It is known that adenosine is distributed abundantly in the whole body, and exhibits a variety of physiological activities on the central nervous system, the cardiac muscle, the kidneys, the smooth muscle, and the like through its receptors (see Non-Patent Document 4).

For example, adenosine $A_1$ antagonists are known to facilitate defecation (*Jpn. J. Pharmacol.*, 1995, Vol. 68, p. 119). Further, involvement of the adenosine $A_{2A}$ receptor, particularly in the central nervous system is known. The antagonists of the adenosine $A_{2A}$ receptor are known to be useful as, for example, therapeutic drugs for Parkinson's disease (see Non-Patent Document 5), or therapeutic drugs for sleep disorder (see Nature *Neuroscience*, 2005, p. 1; Patent Document 2).

There are some reports concerning the relationship between adenosine receptors and migraine (see Non-Patent Documents 6 to 13).

For example, compounds represented by the following formulae (I), (II), (III), (IV), (V), (VI), and (VII) are known as compounds having a selective adenosine $A_{2A}$ receptor antagonistic activity (see Patent Documents 3 to 9, and Non-Patent Documents 14 and 15).

[Chemical Formula 1]

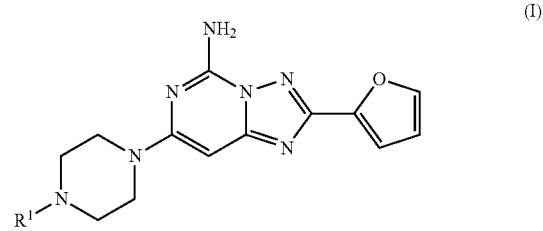

(I)

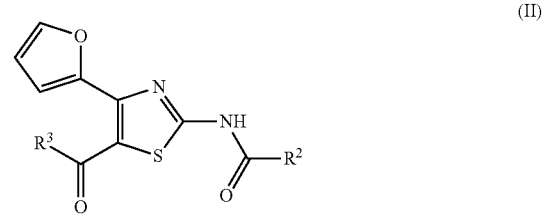

(II)

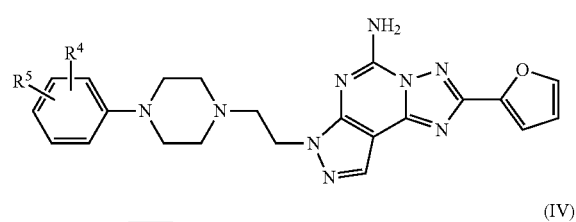

(III)

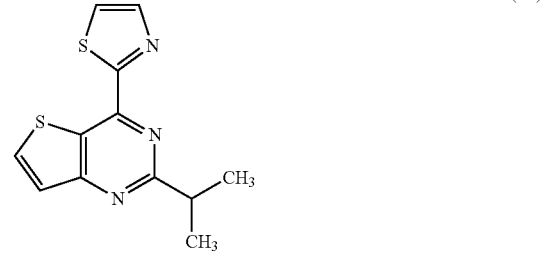

(IV)

-continued

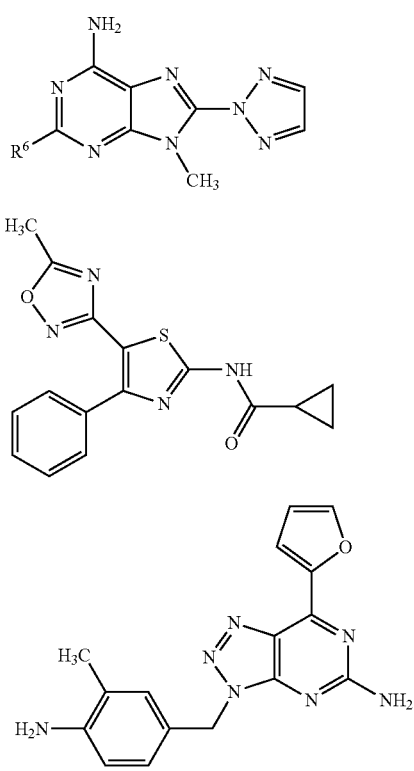

(wherein $R^1$ represents methyl, ethyl, propyl, butyl, or 3-methylbutyl, or any of these groups substituted with hydroxy; $R^2$ represents phenyl, pyridyl, pyrimidinyl, 5,6-dihydro-2H-pyridylmethyl, or tetrahydropyranyloxy, or any of these groups substituted with 1 to 3 substituents selected from a fluorine atom, a chlorine atom, a bromine atom, methyl, ethyl, methoxy, and ethoxy; $R^3$ represents pyridyl or tetrahydropyranyl; $R^4$ and $R^5$ may be the same or different, and each represent a hydrogen atom, a fluorine atom, or 2-methoxyethoxy; and $R^6$ represents methyl, ethyl, propyl, or butyl)

PRIOR ART DOCUMENTS

Patent Documents

Patent Document 1: WO2005/072739
Patent Document 2: WO2007/015528
Patent Document 3: WO98/42711
Patent Document 4: WO00/17201
Patent Document 5: WO2005/063743
Patent Document 6: WO2002/055524
Patent Document 7: WO2003/011864
Patent Document 8: WO2006/032273
Patent Document 9: WO2002/055083

Non-Patent Documents

Non-Patent Document 1: *Proceedings of the National Academy of Sciences of the United States of America*, 2001, Vol. 98, p. 4687
Non-Patent Document 2: *Nature Neuroscience*, 2007, Vol. 10, p. 754
Non-Patent Document 3: *Neurological Research*, 2005, Vol. 27, p. 175
Non-Patent Document 4: *Nature Reviews Drug Discovery*, 2006, Vol. 5, p. 247
Non-Patent Document 5: *Progress in Neurobiology*, 2007, Vol. 83, p. 332
Non-Patent Document 6: *Can. J. Neurol. Sci.*, 1998, Vol. 253, p. 55
Non-Patent Document 7: *Cephalalgia*, 2006, Vol. 26, p. 925
Non-Patent Document 8: *Cephalalgia*, 2007, Vol. 27, p. 177
Non-Patent Document 9: *Brain*, 2002, Vol. 125, p. 1392
Non-Patent Document 10: *Am. J. Physiol.*, 2001, Vol. 281, H2018-H2027
Non-Patent Document 11: *J. Pharmacol. Sci.*, 2004, Vol. 94, p. 100
Non-Patent Document 12: *Pharmacological Reviews*, 1999, Vol. 51, p. 83
Non-Patent Document 13: *Pharmacology & Therapeutics*, 2006, Vol. 112, p. 199
Non-Patent Document 14: *European Journal of Pharmacology*, 1994, Vol. 267, p. 335
Non-Patent Document 15: *Bioorganic & Medicinal Chemistry Letters*, 2007, Vol. 17, p. 1376

SUMMARY OF THE INVENTION

Problems that the Invention is to Solve

An object of the present invention is to provide therapeutic and/or preventive agents for migraine that comprise, as an active ingredient, a compound having an adenosine $A_{2A}$ receptor antagonistic activity or a pharmaceutically acceptable salt thereof, and the like.

Means for Solving the Problems

The present invention relates to the following (1) to (47).

(1) A therapeutic and/or preventive agent for migraine which includes, as an active ingredient, a compound having a selective adenosine $A_{2A}$ receptor antagonistic activity, or a pharmaceutically acceptable salt thereof.

(2) The agent according to claim 1, wherein the compound having a selective adenosine $A_{2A}$ receptor antagonistic activity has an affinity for the adenosine $A_{2A}$ receptor 10 times or higher than that for the adenosine $A_1$ receptor.

(3) The agent according to (1), wherein the compound having a selective adenosine $A_{2A}$ receptor antagonistic activity is a compound selected from the group consisting of compounds represented by the following formulae (I) to (VII).

[Chemical Formula 2]

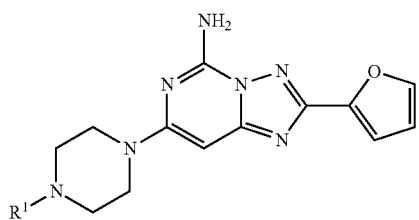

(I)

-continued

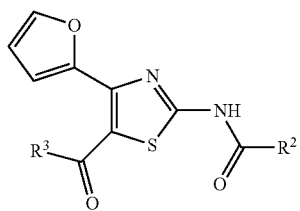
(II)

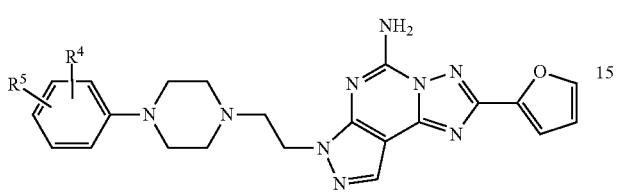
(III)

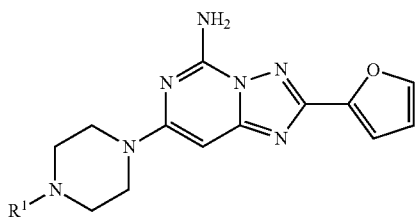
(IV)

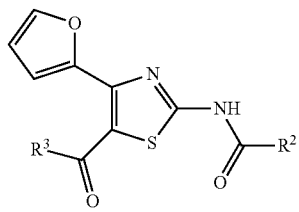
(V)

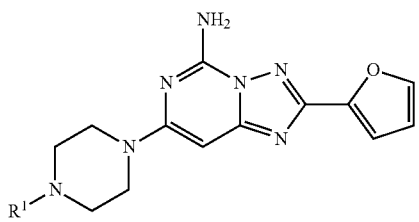
(VI)

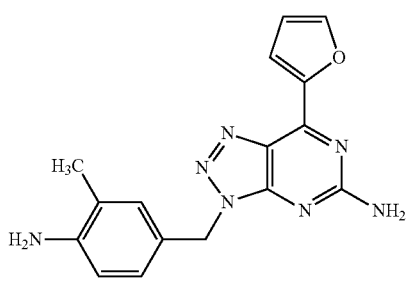
(VII)

(wherein $R^1$ represents methyl, ethyl, propyl, butyl, or 3-methylbutyl, or any of these groups substituted with hydroxy; $R^2$ represents phenyl, pyridyl, pyrimidinyl, 5,6-dihydro-2H-pyridylmethyl, or tetrahydropyranyloxy, or any of these groups substituted with 1 to 3 substituents selected from a fluorine atom, a chlorine atom, a bromine atom, methyl, ethyl, methoxy, and ethoxy; $R^3$ represents pyridyl or tetrahydropyranyl; $R^4$ and $R^5$ may be the same or different, and each represent a hydrogen atom, a fluorine atom, or 2-methoxyethoxy; and $R^6$ represents methyl, ethyl, propyl, or butyl)

(4) The agent according to (1), wherein the compound having a selective adenosine $A_{2A}$ receptor antagonistic activity is a compound represented by the following formula (I) or (II).

[Chemical Formula 3]

(I)

(II)

(wherein $R^1$, $R^2$, and $R^3$ have the same definitions as described above, respectively)

(5) The agent according to (1), wherein the compound having a selective adenosine $A_{2A}$ receptor antagonistic activity is a compound represented by the following formula (I).

[Chemical Formula 4]

(I)

(wherein $R^1$ has the same definition as described above)

(6) The agent according to (5), wherein $R^1$ is ethyl which may be substituted with hydroxy, or 3-methylbutyl which may be substituted with hydroxy.

(7) The agent according to (1), wherein the compound having a selective adenosine $A_{2A}$ receptor antagonistic activity is a compound represented by the following formula (II).

[Chemical Formula 5]

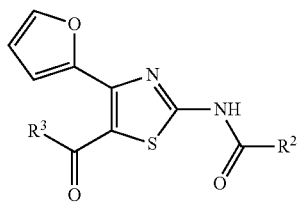
(II)

(wherein R² and R³ have the same definitions as described above, respectively)

(8) The agent according to (7), wherein $R^3$ is pyridyl.

(9) The agent according to (7), wherein $R^3$ is tetrahydropyranyl.

(10) A method for treating and/or preventing migraine, which comprises administering an effective amount of a compound having a selective adenosine $A_{2A}$ receptor antagonistic activity or a pharmaceutically acceptable salt thereof.

(11) The method according to (10), wherein the compound having a selective adenosine $A_{2A}$ receptor antagonistic activity has an affinity for the adenosine $A_{2A}$ receptor 10 times or higher than that for the adenosine $A_1$ receptor.

(12) The method according to (10), wherein the compound having a selective adenosine $A_{2A}$ receptor antagonistic activity is a compound selected from the group consisting of compounds represented by the following formulae (I) to (VII).

[Chemical Formula 6]

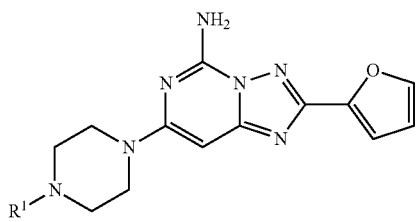
(I)

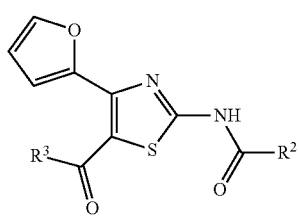
(II)

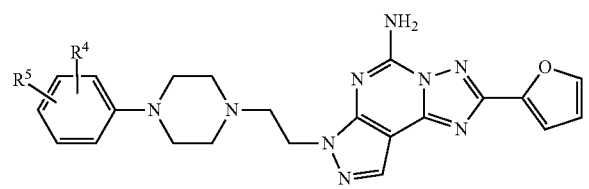
(III)

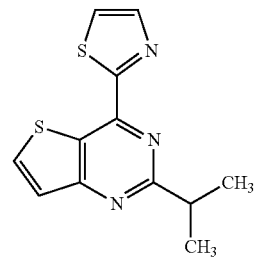
(IV)

(V)

(VI)

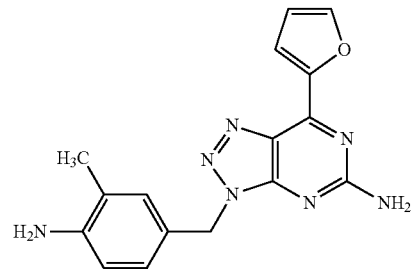

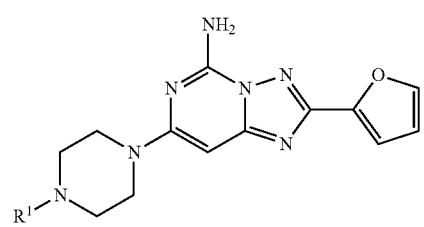
(VII)

(wherein $R^1$, $R^2$, $R^3$, $R^4$, $R^5$, and $R^6$ have the same definitions as described above, respectively)

(13) The method according to (10), wherein the compound having a selective adenosine $A_{2A}$ receptor antagonistic activity is a compound represented by the following formula (I) or (II).

[Chemical Formula 7]

(I)

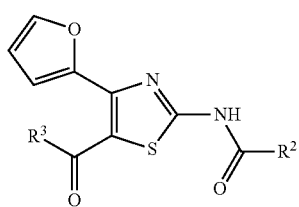

(II)

(wherein R¹, R², and R³ have the same definitions as described above, respectively)

(14) The method according to (10), wherein the compound having a selective adenosine $A_{2A}$ receptor antagonistic activity is a compound represented by the following formula (I).

[Chemical Formula 8]

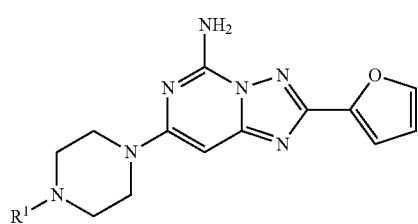

(I)

(wherein R¹ has the same definition as described above)

(15) The method according to (14), wherein R¹ is ethyl which may be substituted with hydroxy, or 3-methylbutyl which may be substituted with hydroxy.

(16) The method according to (10), wherein the compound having a selective adenosine $A_{2A}$ receptor antagonistic activity is a compound represented by the following formula (II).

[Chemical Formula 9]

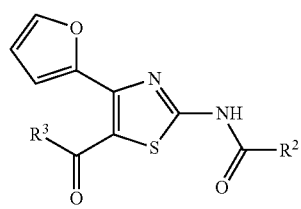

(II)

(wherein R² and R³ have the same definitions as described above, respectively)

(17) The method according to (16), wherein R³ is pyridyl.

(18) The method according to (16), wherein R³ is tetrahydropyranyl.

(19) Use of a compound having a selective adenosine $A_{2A}$ receptor antagonistic activity or a pharmaceutically acceptable salt thereof for the manufacture of a therapeutic and/or preventive agent for migraine.

(20) The use according to (19), wherein the compound having a selective adenosine $A_{2A}$ receptor antagonistic activity has an affinity for the adenosine $A_{2A}$ receptor 10 times or higher than that for the adenosine $A_1$ receptor.

(21) The use according to (19), wherein the compound having a selective adenosine $A_{2A}$ receptor antagonistic activity is a compound selected from the group consisting of compounds represented by the following formulae (I) to (VII).

[Chemical Formula 10]

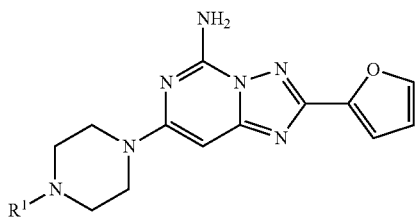

(I)

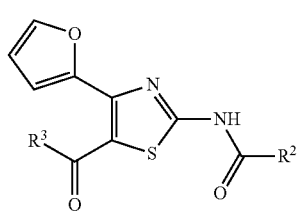

(II)

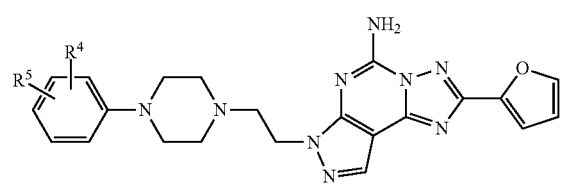

(III)

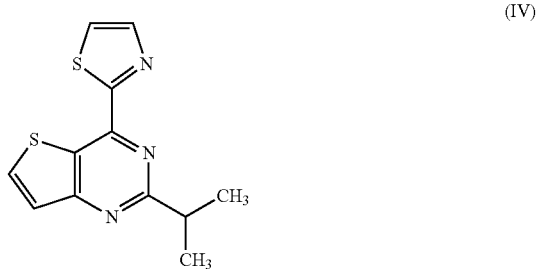

(IV)

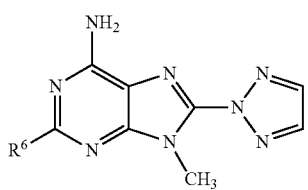

(V)

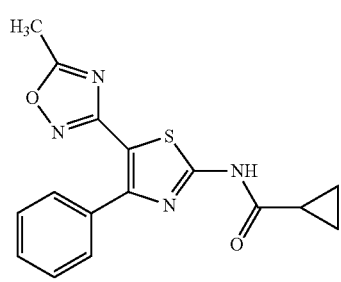

(VI)

-continued

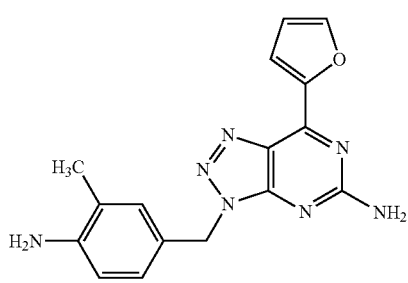

(VII)

(wherein $R^1$, $R^2$, $R^3$, $R^4$, $R^5$, and $R^6$ have the same definitions as described above, respectively)

(22) The use according to (19), wherein the compound having a selective adenosine $A_{2A}$ receptor antagonistic activity is a compound represented by the following formula (I) or (II).

[Chemical Formula 11]

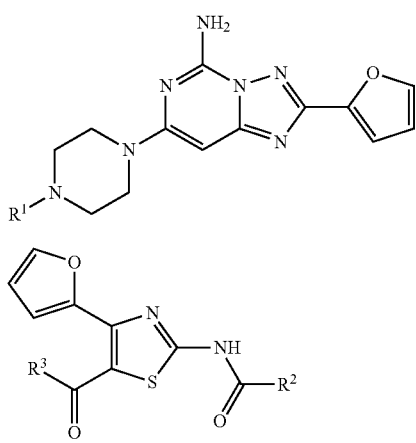

(I)

(II)

(wherein $R^1$, $R^2$, and $R^3$ have the same definitions as described above, respectively)

(23) The use according to (19), wherein the compound having a selective adenosine $A_{2A}$ receptor antagonistic activity is a compound represented by the following formula (I).

[Chemical Formula 12]

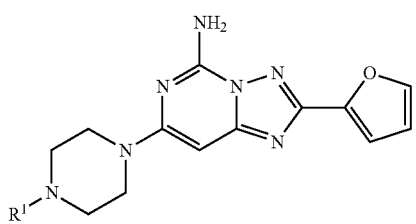

(I)

(wherein $R^1$ has the same definition as described above)

(24) The use according to (23), wherein $R^1$ is ethyl which may be substituted with hydroxy, or 3-methylbutyl which may be substituted with hydroxy.

(25) The use according to (19), wherein the compound having a selective adenosine $A_{2A}$ receptor antagonistic activity is a compound represented by the following formula (II).

[Chemical Formula 13]

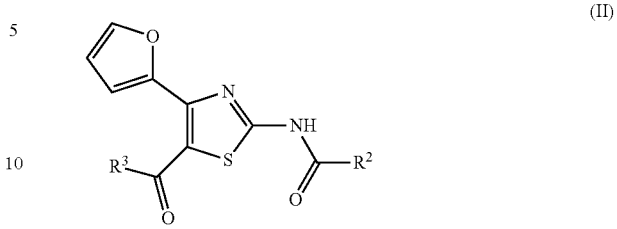

(II)

(wherein $R^2$ and $R^3$ have the same definitions as described above, respectively)

(26) The use according to (25), wherein $R^3$ is pyridyl.

(27) The use according to (25), wherein $R^3$ is tetrahydropyranyl.

(28) A compound having a selective adenosine $A_{2A}$ receptor antagonistic activity or a pharmaceutically acceptable salt thereof for use in the treatment and/or prevention of migraine.

(29) A compound or a pharmaceutically acceptable salt thereof for use in the treatment and/or prevention of migraine, wherein the compound has an affinity for the adenosine $A_{2A}$ receptor 10 times or higher than that for the adenosine $A_1$ receptor.

(30) A compound or a pharmaceutically acceptable salt thereof for use in the treatment and/or prevention of migraine, wherein the compound is selected from the group consisting of compounds represented by the following formulae (I) to (VII).

[Chemical Formula 14]

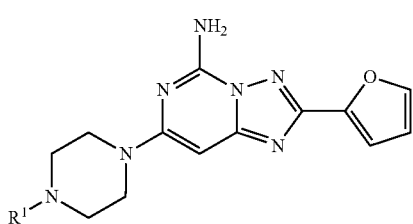

(I)

(II)

(III)

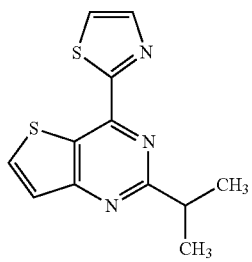

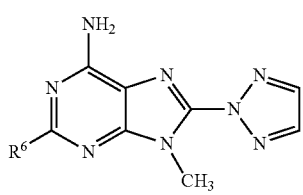

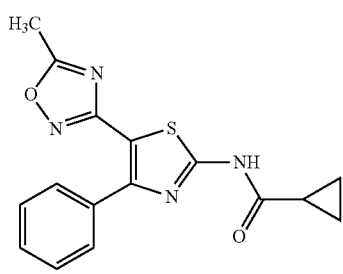

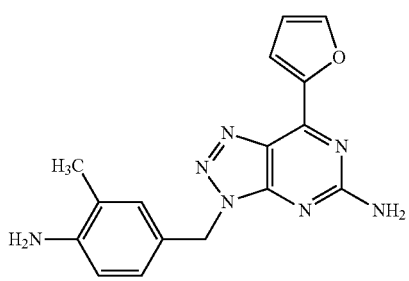

(wherein $R^1$, $R^2$, $R^3$, $R^4$, $R^5$, and $R^6$ have the same definitions as described above, respectively)

(31) A compound or a pharmaceutically acceptable salt thereof for use in the treatment and/or prevention of migraine, wherein the compound is represented by the following formula (I) or (II).

[Chemical Formula 15]

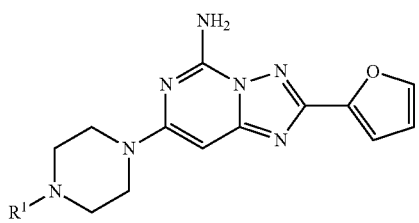

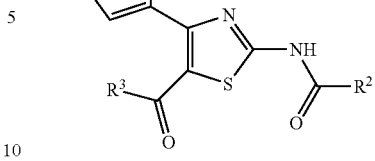

(wherein $R^1$, $R^2$, and $R^3$ have the same definitions as described above, respectively)

(32) A compound or a pharmaceutically acceptable salt thereof for use in the treatment and/or prevention of migraine, wherein the compound is represented by the following formula (I).

[Chemical Formula 16]

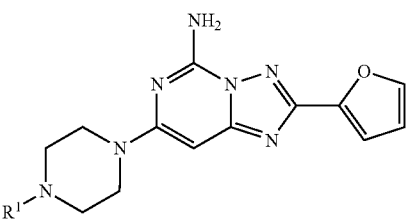

(wherein $R^1$ has the same definition as described above)

(33) The compound or a pharmaceutically acceptable salt thereof according to (32), wherein $R^1$ is ethyl which may be substituted with hydroxy, or 3-methylbutyl which may be substituted with hydroxy.

(34) A compound or a pharmaceutically acceptable salt thereof for use in the treatment and/or prevention of migraine, wherein the compound is represented by the following formula (II).

[Chemical Formula 17]

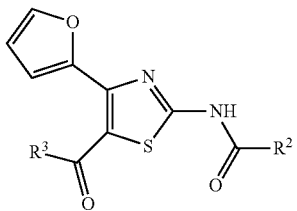

(wherein $R^2$ and $R^3$ have the same definitions as described above, respectively)

(35) The compound or a pharmaceutically acceptable salt thereof according to (34), wherein $R^3$ is pyridyl.

(36) The compound or a pharmaceutically acceptable salt thereof according to (34), wherein $R^3$ is tetrahydropyranyl.

(37) The agent according to any one of (1) to (9), wherein the migraine is migraine with aura.

(38) The agent according to any one of (1) to (9), wherein the migraine is migraine without aura.

(39) A therapeutic and/or preventive agent for headache which comprises the compound or a pharmaceutically acceptable salt thereof of any one of (1) to (9).

(40) The method according to any one of (10) to (18), wherein the migraine is migraine with aura.

(41) The method according to any one of (10) to (18), wherein the migraine is migraine without aura.

(42) The use according to anyone of (19) to (27), wherein the migraine is migraine with aura.

(43) The use according to anyone of (19) to (27), wherein the migraine is migraine without aura.

(44) The compound or a pharmaceutically acceptable salt thereof according to any one of (28) to (36), wherein the migraine is migraine with aura.

(45) The compound or a pharmaceutically acceptable salt thereof according to any one of (28) to (36), wherein the migraine is migraine without aura.

(46) A method for treating and/or preventing headache, which comprises the compound or a pharmaceutically acceptable salt thereof of any one of (1) to (9).

(47) Use of the compound or a pharmaceutically acceptable salt thereof of any one of (1) to (9) for the manufacture of a therapeutic and/or preventive agent for headache.

Effects of the Invention

The present invention can provide therapeutic and/or preventive agents for migraine which comprise, as an active ingredient, a compound having a selective adenosine $A_{2A}$ receptor antagonistic activity or a pharmaceutically acceptable salt thereof, and the like.

MODE FOR CARRYING OUT THE INVENTION

In the following, the compound represented by general formula (I) will also be referred to as Compound (I). The compounds having other formula numbers are also referred to in the same manner.

The compound having a selective adenosine $A_{2A}$ receptor antagonistic activity of the present invention is preferably a compound that has a strong antagonistic activity for the adenosine $A_{2A}$ receptor from among various subtypes (for example, adenosine $A_1$, $A_{2A}$, $A_{2B}$, and $A_3$ receptors) of the adenosine receptors.

Accordingly, a compound having strong affinity for the adenosine $A_{2A}$ receptor is preferred as the compound having a selective adenosine $A_{2A}$ receptor antagonistic activity of the present invention. For example, the compound is preferably a compound that has 50% or more inhibitory effect at a test compound concentration of $3\times10^{-8}$ mol/L, more preferably a compound having 50% or more inhibitory effect at a test compound concentration of $1\times10^{-8}$ mol/L, further preferably a compound having 50% or more inhibitory effect at a test compound concentration of $3\times10^{-9}$ mol/L, even more preferably a compound having 50% or more inhibitory effect at a test compound concentration of $1\times10^{-9}$ mol/L, as measured by the adenosine $A_{2A}$ receptor binding test described in Test Example 1 below. Further, the compound is preferably a compound having an inhibitory effect with an inhibition constant (Ki value; obtained in the same test) of 30 nmol/L or less, more preferably a compound having an inhibitory effect with an inhibition constant of 10 nmol/L or less, further preferably a compound having an inhibitory effect with an inhibition constant of 3 nmol/L or less, even more preferably a compound having an inhibitory effect with an inhibition constant of 1 nmol/L or less.

Further, the compound having a selective adenosine $A_{2A}$ receptor antagonistic activity used in the present invention is preferably a compound having selective affinity for the adenosine $A_{2A}$ receptor from among various subtypes of the adenosine receptors. For example, a compound having a higher affinity for the adenosine $A_{2A}$ receptor than for the adenosine $A_1$ receptor is preferable. Specifically, for example, the compound is preferably a compound having 5 times or more affinity, more preferably 10 times or more affinity, further preferably 50 times or more affinity, even more preferably 100 times or more affinity, most preferably 500 times or more affinity for the adenosine $A_{2A}$ receptor than that for the adenosine $A_1$ receptor.

The affinity can be determined according to the conventional manner, for example, according to the method of Test Example 1 below, or the methods described in, for example, *Naunyn Schmiedebergs Arch Pharmacol.* 1987, 355 (1), p. 59-63; *Naunyn Schmiedebergs Arch Pharmacol.* 1987, 355 (2), p. 204-210; or *Br. J. Pharmacol.* 1996, 117 (8), p. 1645-1652.

The compounds represented by the following formulae (I) to (VII) or pharmaceutically acceptable salts thereof are more specific examples of the compound having a selective adenosine $A_{2A}$ receptor antagonistic activity of the present invention.

[Chemical Formula 18]

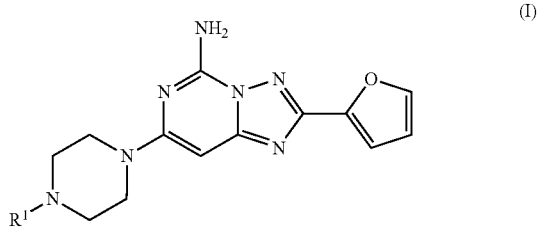

(I)

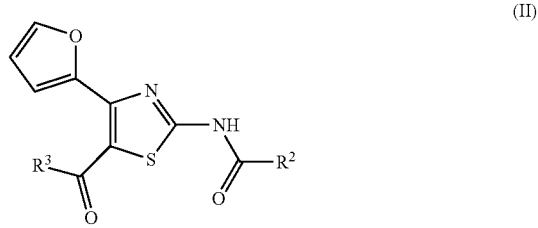

(II)

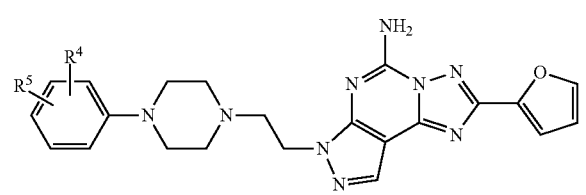

(III)

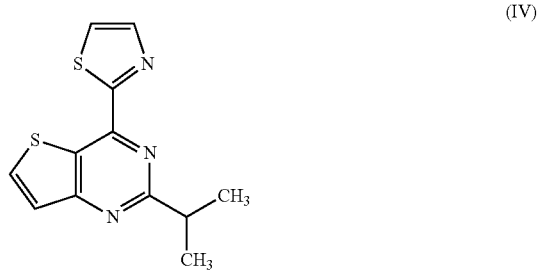

(IV)

-continued (V)
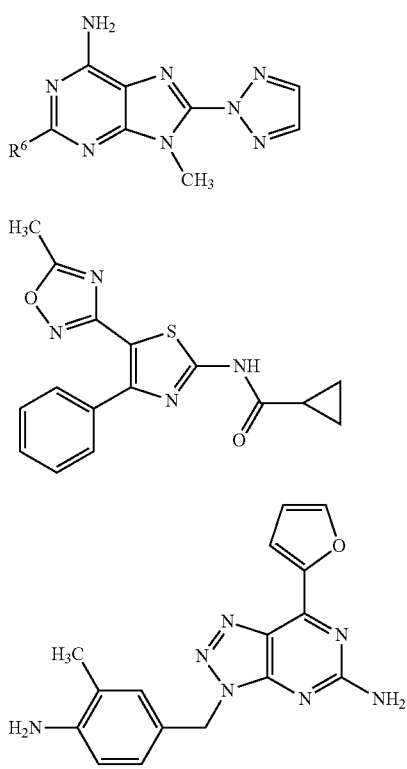

(VI)

(VII)

(wherein $R^1$, $R^2$, $R^3$, $R^4$, $R^5$, and $R^6$ have the same definitions as described above, respectively)

The compound having a selective adenosine $A_{2A}$ receptor antagonistic activity of the present invention is more preferably a compound represented by the following formula (I) or (II), or a pharmaceutically acceptable salt thereof.

[Chemical Formula 19]

(I)

(II)
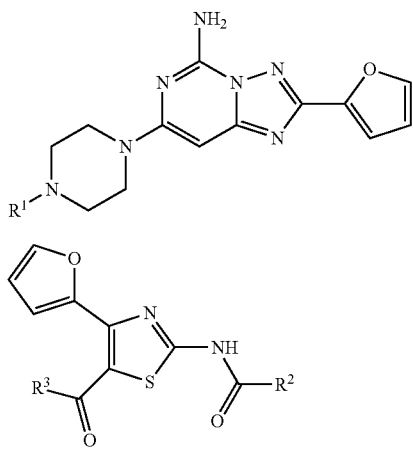

(wherein $R^1$, $R^2$, and $R^3$ have the same definitions as described above, respectively)

More specifically, for example, the compound represented by the following formula (IA), (IB), (IIA), (IIB), (IIC), (IID), (IIIA), (IIIB), (IV), (VA), (VI), or (VII), or a pharmaceutically acceptable salt thereof is preferable, and the compound represented by the following formula (IA), (IB), (IIA), (IIB), (IIC), or (IID) is more preferable.

[Chemical Formula 20]

(IA)
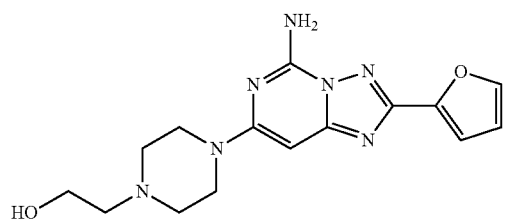

(IB)
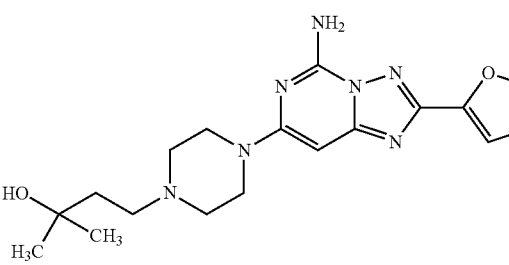

(IIA)
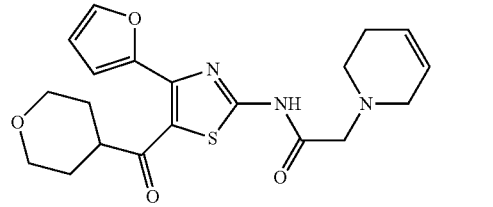

(IIB)
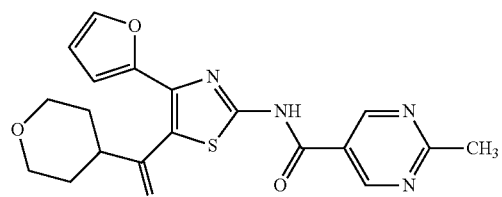

(IIC)
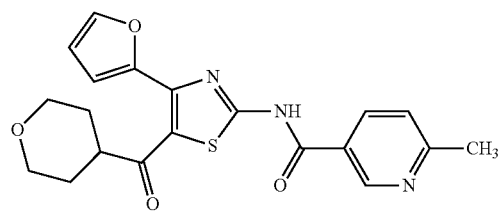

(IID)
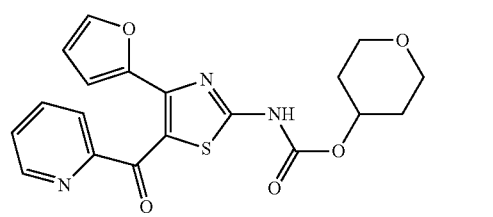

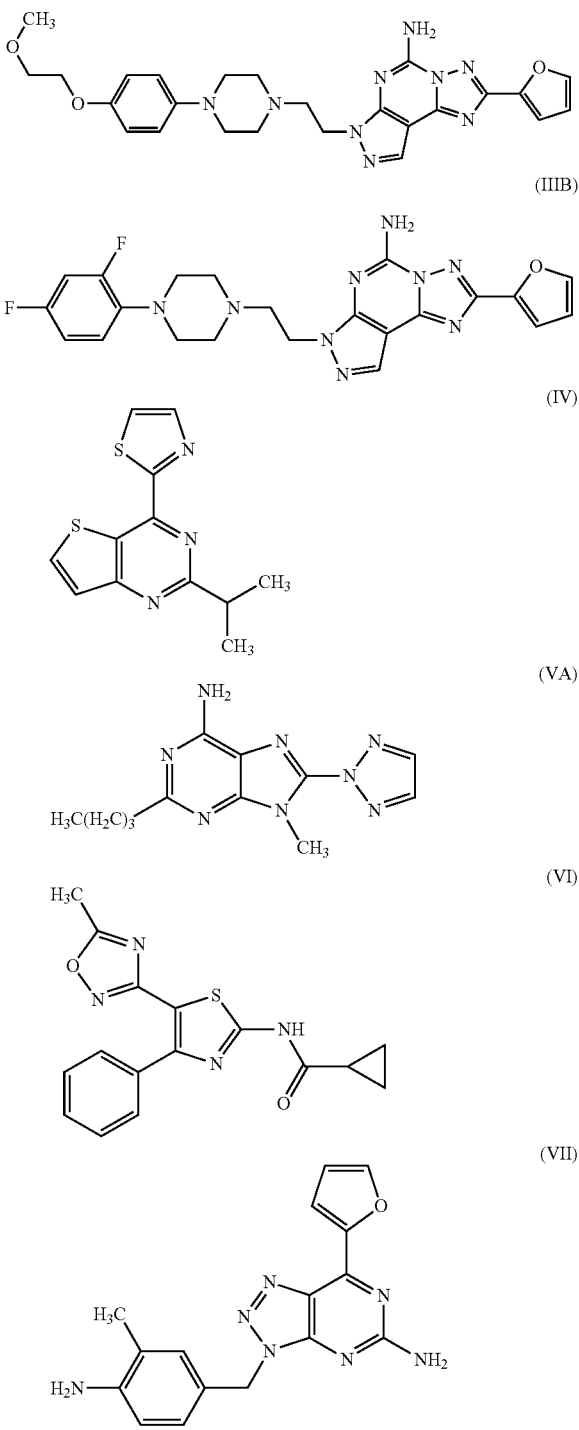

The pharmaceutically acceptable salts of the compound having a selective adenosine $A_{2A}$ receptor antagonistic activity used in the present invention include, for example, pharmaceutically acceptable acid addition salts, metal salts, ammonium salts, organic amine addition salts, amino acid addition salts, and the like.

The pharmaceutically acceptable acid addition salts of the compound having a selective adenosine $A_{2A}$ receptor antagonistic activity used in the present invention include, for example, inorganic acid salts such as hydrochloride, hydrobromate, nitrate, sulfate, and phosphate; organic acid salts such as acetate, oxalate, maleate, fumarate, citrate, benzoate, and methane sulfonate, and the like. Examples of the pharmaceutically acceptable metal salts include alkali metal salts such as a sodium salt, and a potassium salt; alkaline earth metal salts such as a magnesium salt, and a calcium salt; an aluminum salt; a zinc salt, and the like. Examples of the pharmaceutically acceptable ammonium salts include salts of ammonium, tetramethylammonium, and the like. Examples of the pharmaceutically acceptable organic amine addition salts include addition salts of morpholine, piperidine, or the like. Examples of the pharmaceutically acceptable amino acid addition salts include addition salts of lysine, glycine, phenylalanine, aspartic acid, glutamic acid, or the like.

The compound having a selective adenosine $A_{2A}$ receptor antagonistic activity or a pharmaceutically acceptable salt thereof used in the present invention can be produced according to the conventionally known methods, respectively. For example, compound (I) can be produced according to the methods described in, for example, WO98/42711, WO00/17201, or the like. Compound (II) can be produced according to the methods described in, for example, WO2005/063743 or the like. Compound (III) can be produced according to the methods described in, for example, WO2001/092264 or the like. Compound (IV) can be produced according to the methods described in, for example, WO2002/055524 or the like. Compound (V) can be produced according to the methods described in, for example, WO2003011864 or the like. Compound (VI) can be produced according to the methods described in, for example, WO2006/032273 or the like. Compound (VII) can be produced according to the methods described in, for example, WO2002/055083 or the like.

The compounds having a selective adenosine $A_{2A}$ receptor antagonistic activity used in the present invention may exist as stereoisomers such as geometrical isomers or optical isomers, or tautomers. These and all other possible isomers and mixtures thereof can also be used for, for example, the therapeutic and/or preventive agents for migraine of the present invention.

To obtain a salt of the compound having a selective adenosine $A_{2A}$ receptor antagonistic activity used in the present invention, when the compound is obtained in the form of a salt, it may be purified as it is. Further, when the compound is obtained in a free form, the compound may be dissolved or suspended in a suitable solvent, followed by addition of an acid or a base to form a salt. Then, the resulting salt may be isolated and purified.

The compounds having a selective adenosine $A_{2A}$ receptor antagonistic activity or a pharmaceutically acceptable salt thereof used in the present invention may exist in the form of an adduct with water or various solvents. Such adducts can also be used for, for example, the therapeutic and/or preventive agents for migraine, and the methods for treating and/or preventing migraine of the present invention.

Examples of disorders that can be treated and/or prevented by, for example, the therapeutic and/or preventive agents for migraine, and the methods for treating and/or preventing migraine of the present invention include various types of migraine presented in, for example, *The International Classification of Headache Disorders, 2nd edition (ICHD-II)* (The International Headache Society (IHS) 2003). Specific examples include migraine without aura, migraine with aura, childhood periodic syndromes (with frequent transition to migraine), retinal migraine, complications of migraine, probable migraine, and the like. These include migraines in women during menstruation such as menstrual migraine, migraines seen in the young such as childhood migraine, and the like.

The following specifically describes the biological activity of representative compounds having a selective adenosine $A_{2A}$ receptor antagonistic activity, based on Test Examples.

Test Example 1

Adenosine Receptor Binding Activity (1) Adenosine $A_{2A}$ Receptor Binding Test The test is performed according to the method of Bruns et al. (*Molecular Pharmacology*, Vol. 29, p. 331, 1986).

Rat (SD rat, Japan SLC, Inc.) striatum is suspended in mL of ice-cooled tris(hydroxymethyl)-aminomethane hydrochloride (Tris HCl) buffer (50 mmol/L, pH 7.7), using a Polytron homogenizer (Kinematica, Inc.). The suspension is centrifuged (48,000×g, 20 minutes) and the resulting precipitate is resuspended by adding the same amount of Tris HCl buffer (50 mmol/L) thereto, followed by centrifugation under the same conditions. The resulting final precipitate is suspended in Tris HCl buffer (50 mmol/L) [containing magnesium chloride (10 mmol/L), and adenosine deaminase (0.02 units/mg tissue) (Sigma)] to prepare the suspension at the tissue concentration of 5 mg (wet weight)/mL.

To 100 μl of the purified cell suspension, 80 μL of tritium-labeled CGS-21680 {$^3$H-2-[p-(2-carboxyethyl)phenethylamino]-5'-(N-ethylcarbox amido)adenosine: 40 Ci/mmol; New England Nuclear [*The Journal of Pharmacology and Experimental Therapeutics*, Vol. 251, p. 888, 1989]} (final concentration of 6.0 mmol/L), and 20 μL of the test compound solution (dimethylsulfoxide solution of test compound diluted with Tris HCl buffer) are added. The mixture is allowed to stand at 25° C. for 120 minutes, followed by rapid suction filtration using glass-fiber filter paper (GF/C; Whatman), and then immediately washed three times with 200 μL of ice-cooled Tris HCl buffer (50 mmol/L). The glass-fiber filter paper is then placed in a vial, and MicroScinti liquid (PKI) is added. Then, the radioactivity is measured with a TopCount (PerkinElmer).

Percentage inhibition of adenosine $A_{2A}$ receptor binding ($^3$H-CGS21680 binding) by the test compound can be calculated by the following equation.

$$\text{Percentage Inhibition (\%)} = \left(1 - \frac{\text{Amount of binding in the presence of medicament} - \text{amount of non-specific binding}}{\text{Total amount of binding} - \text{amount of non-specific binding}}\right) \times 100 \quad \text{[Equation 1]}$$

In the equation, the total amount of binding refers to the bound radioactivity of $^3$H-CGS21680 in the absence of the test compound. The amount of non-specific binding refers to the bound radioactivity of $^3$H-CGS21680 in the presence of 100 mol/L of cyclopentyladenosine (CPA; Sigma). The amount of binding in the presence of medicament refers to the bound radioactivity of $^3$H-CGS21680 in the presence of the test compound.

In the above test, the percentage inhibition for the adenosine $A_{2A}$ receptor at different concentrations of the test compound or a pharmaceutically acceptable salt thereof, and the test compound concentration at which the test compound inhibits binding by 50% ($IC_{50}$) can be calculated by appropriately adjusting the concentration of the test compound.

The inhibition constant (Ki value) of the test compound for the adenosine $A_{2A}$ receptor binding can be calculated according to the following equation.

$$Ki = IC_{50}/(1 + L/Kd) \quad \text{[Equation 2]}$$

In the equation, L denotes the concentration of the $^3$H-CGS21680 used in the test, and Kd is the dissociation constant of the $^3$H-CGS21680 used in the test.

Instead of $^3$H-CGS21680, for example, $^3$H-SCH58261 [$^3$H-5-amino-7-(2-phenylethyl)-2-(2-furyl)pyrazolo[4,3-e]-1,2,4-triazolo[1,5-c]pyrimidine (synthesized by GE healthcare bio-sciences)] may be used.

The affinity of the test compound for the adenosine $A_{2A}$ receptor can be confirmed by the foregoing test.

(2) Adenosine $A_1$ Receptor Binding Test

The inhibition constant (Ki value) of the test compound for the adenosine $A_1$ receptor can be calculated in the same manner as in (1), using the materials below.

Specifically, for example, rat $A_1$ receptor-expressing cell membrane (PerkinElmer) is used, and, for example, tritium-labeled CHA [$N^6$-cyclohexyladenosine (PerkinElmer)] is used as the labeled compound. For the measurement of non-specific binding amount, $^3$H-CHA bound radioactivity is measured in the presence of, for example, 10 μmol/L DPCPX [1,3-dipropyl-8-cyclopentylxanthine (Sigma)].

The affinity of the test compound for the adenosine $A_1$ receptor can be confirmed by the foregoing test.

By the foregoing tests (1) and (2), the selective affinities of the compounds (I) to (VII) and the like for the adenosine $A_{2A}$ receptor can be confirmed.

Some of the examples of the affinities for the adenosine $A_{2A}$ receptor as determined by the foregoing test with the compounds having a selective adenosine $A_{2A}$ receptor antagonistic activity or pharmaceutically acceptable salts thereof used in the present invention are presented below.

TABLE 1

| Compound number | Percentage inhibition for adenosine $A_{2A}$ receptor binding ($^3$H-CGS21680 binding) |
|---|---|
| (IA) | 75%* |
| (IB) | 81%** |

*Percentage inhibition at 100 nmol/L of compound (IA)
*Percentage inhibition at 1,000 nmol/L of compound (IB)

Test Example 2

Adenosine Receptor Binding Activity (2)

(1) Human Adenosine $A_{2A}$ Receptor Binding Test

The test is performed according to the method of, for example, Varani et al. [*British Journal of Pharmacology*, Vol. 117, p. 1693 (1996)].

Specifically, for example, human recombinant adenosine $A_{2A}$ receptors are expressed in HEK-293 cells. The cell membranes of the receptor-expressing cells are collected, and a cell membrane suspension is prepared. After dilution with Tris HCl buffer, tritium-labeled CGS-21680 (50 mmol/L) and a test compound solution (dimethylsulfoxide solution of the test compound) are added to the cell membrane suspension for binding to the receptors. After the reaction, the mixture is subjected to rapid suction filtration using glass-fiber filter paper, and the radioactivity of the glass-fiber filter paper is measured. In this way, the percentage inhibition of the test compound for the adenosine $A_{2A}$ receptor binding ($^3$H-CGS21680 binding) can be determined.

Percentage inhibition can be calculated according to the following equation.

$$\text{Percentage Inhibition (\%)} = \left(1 - \frac{\begin{array}{c}\text{Amount of binding in}\\ \text{the presence of medicament} -\\ \text{amount of non-specific binding}\end{array}}{\text{Total amount of binding} - \text{amount of non-specific binding}}\right) \times 100 \quad \text{[Equation 3]}$$

In the equation, the total amount of binding refers to the bound radioactivity of $^3$H-CGS21680 in the absence of the test compound. The amount of non-specific binding refers to the bound radioactivity of $^3$H-CGS21680 in the presence of 50 µmol/L 5'-N-ethyl carboxamide adenosine (NECA) or 100 µmol/L CPA. The amount of binding in the presence of medicament refers to the bound radioactivity of $^3$H-CGS21680 in the presence of the test compound.

In the above test, the percentage inhibition for the human adenosine $A_{2A}$ receptor at different concentrations of the test compound or a pharmaceutically acceptable salt thereof, and the test compound concentration at which the test compound inhibits binding by 50% ($IC_{50}$) can be calculated by appropriately adjusting the concentration of the test compound.

The inhibition constant (Ki value) of the test compound for the human adenosine $A_{2A}$ receptor binding can be calculated according to the following equation.

$$Ki = IC_{50}/(1+L/Kd) \quad \text{[Equation 4]}$$

In the equation, L denotes the concentration of the $^3$H-CGS21680 used in the test, and Kd is the dissociation constant of the $^3$H-CGS21680 used in the test.

Instead of $^3$H-CGS21680, for example, $^3$H-SCH58261 may be used.

(2) Human Adenosine $A_1$ Receptor Binding Test

The inhibition constant (Ki value) of the test compound for the human adenosine $A_1$ receptor can be calculated in the same manner as in (1), using the materials below.

Specifically, for example, human $A_1$ receptor-expressing CHO cell membranes are used, and, for example, tritium-labeled DPCPX is used as the labeled compound. The amount of non-specific binding can be determined by measuring the $^3$H-DPCPX bound radioactivity in the presence of, for example; 100 µmol/L R(−)-PIA((−)-N$^6$-2-phenylisopropyl adenosine). The affinity of the test compound for the human adenosine $A_1$ receptor can be confirmed in this manner.

By the foregoing tests (1) and (2), the selective affinities of the compounds (I) to (VII) and the like for the human adenosine $A_{2A}$ receptor can be confirmed.

(3) Affinity of the Compound or Pharmaceutically Acceptable Salt Thereof Used in the Present Invention for Human Adenosine Receptor Some of the examples of the affinities of the compounds (IIA) to (IID) for the human adenosine $A_1$ receptor and human adenosine $A_{2A}$ receptor are presented below. Note that the test results below are the results of measurements performed by MDS Pharma Services Inc. according to the foregoing methods.

TABLE 2

| | Affinity for Adenosine Receptors | |
|---|---|---|
| Compound number | Percentage inhibition for human adenosine $A_{2A}$ receptor binding ($^3$H-CGS21680 binding)* | Percentage inhibition for human adenosine $A_1$ receptor binding ($^3$H-DPCPX binding)* |
| (IIA) | 92% | 14% |
| (IIB) | 98% | 4% |
| (IIC) | 88% | 29% |
| (IID) | 100% | 28% |

*Percentage inhibition at 100 nmol/L of compound

The selective affinities of the compounds (IIA) to (IID) for the human adenosine $A_{2A}$ receptor were confirmed by the foregoing tests.

Test Example 3

Cerebral Vasoconstriction Effect

Dogs were anesthetized by intravenous administration of sodium pentobarbital, exsanguinated by decapitation and subjected to craniotomy.

The basilar arteries were removed, and ring specimens of cerebral vascular smooth muscle measuring about 2 mm in width were prepared. Each ring specimen was fixed to an injection needle (cut into a 2-mm piece) with a silk thread. The injection needle was fixed to a holder installed in an Easy Magnus Device (Model: UC-2; Kishimoto Medical Instruments), and the specimen was allowed to stabilize for 60 minutes or more under a resting tension of 0.2 g (1.96 mN) in a 37° C. nutritive solution. The cerebral vascular smooth muscle was relaxed with 2 µL of a 10 mmol/L adenosine aqueous solution added to the bath (2 mL) of the Easy Magnus Device, and the test compound was added cumulatively as a 1-µL solution of 0.2 mmol/L dimethylsulfoxide, a 1-µL solution of 0.4 mmol/L dimethylsulfoxide, and a 0.7-µL solution of 2 mmol/L dimethylsulfoxide in this order (test compound-added group). Separately, in the same manner as in the test compound-administered group, dimethylsulfoxide alone was cumulatively added in place of the test compound (solvent-added group). The contraction of the cerebral vascular smooth muscle was then recorded on a recorder (Yokogawa Electric Corporation) from a transducer (Nihon Kohden Corporation) connected to the holder, to which the specimen was fixed, via a strain pressure amplifier (Nihon Kohden Corporation) (n=6).

Relaxation of the removed cerebral vascular smooth muscle by the addition of adenosine was confirmed. The cerebral vasoconstriction effect was determined as the percentage inhibition (%) of the adenosine-induced cerebral vascular smooth muscle relaxation, and comparison was made between the test compound-added group and the solvent-added group.

The test demonstrates that the compound having a selective adenosine $A_{2A}$ receptor antagonistic activity or a pharmaceutically acceptable salt thereof of the present invention can suppress the adenosine-induced cerebrovascular relaxation.

The result of the foregoing test confirmed that the compound-added group (IIC; 10 nmol/L) had a significant suppressing effect (percentage inhibition: 97.4±1.8%) over the solvent-added group (percentage inhibition: 0.6±7.6%). The effect was also confirmed in, for example, compound (IB).

The result therefore suggests that the compounds having a selective adenosine $A_{2A}$ receptor antagonistic activity, such as compounds (I) to (VII) and the like, or pharmaceutically acceptable salts thereof are useful as therapeutic and/or preventive agents for migraine.

Test Example 4

Effect on Cerebral Blood Flow Increase by Electrostimulation of Anesthetized Rat Trigeminal Nerve The test was performed according to the method of Tsukahara et al. [*Cerebral Blood Flow and Metabolism*, Vol. 14, P. 8 (2002)].

SD rats (male, Charles River) were anesthetized by intraperitoneal administration of sodium pentobarbital (60 mg/kg; Tokyo Chemical Industry Co., Ltd.). The cervical region of each rat was cut open, and a tracheal catheter was inserted. A blood-pressure measuring catheter was inserted to the right femoral artery. The rat was fixed to a stereotaxic instrument (stereotaxic instrument for rats; Summit Medical), and the body temperature was maintained at 37° C. on a body temperature-maintaining heating pad (Model: CMA/150; Carnegie Medicine). An electric drill (Model: C-201; Urawa Kogyo) was used to form a cranial window with a diameter of 5 mm (cranial window central coordinate AP: −1.5, L: −1, H: −1.5), and the cerebral blood flow was measured. A Laser Doppler Flowmeter (Model: ALF-2100; Advance) was used for the measurement of cerebral blood flow. Each mean blood pressure was recorded on a recorder (Model: PE3066; Yokogawa Electric Corporation) through measurement from a pressure transducer (Model: DX-312, Nihon Kohden Corporation) via a strain pressure amplifier (Model: AP-612GA; Nihon Kohden Corporation), using a polygraph system (Model: RM6000; Nihon Kohden Corporation). Arterial blood gas partial pressure (pH, $PaO_2$, $PaCO_2$) was measured using a laptop hemanalysis system (Model: AVL-OPTI-CCA; Sysmex).

The distal portion of the trigeminal nerve was detached, and fixed to a stimulation bipolar electrode (tungsten line, 5 mm in width). A rectangular wave (30 Hz, 2-8 V) that showed the maximum blood flow increase was set for the electrostimulation applied via the trigeminal nerve, using a bio-electrostimulator (Model: SEN-3301; Nihon Kohden Corporation) and an isolator (Model: SS-201J; Nihon Kohden Corporation). The electrostimulation of the trigeminal nerve was applied for 30 seconds at 5-minute intervals, and the test compound or the solvent was given after the stimulated blood flow increase became stable. Changes in cerebral blood flow by electrostimulation after 10, 20, and 30 minutes from the administration were measured, and the effects of the test compound and the solvent were compared.

When the compound having a selective adenosine $A_{2A}$ receptor antagonistic activity of the present invention was used as the test compound, the increase in the intracranial cerebral blood flow by the trigeminal nerve activation was suppressed in the test compound-administered group.

It is considered from this result that the compounds having a selective adenosine $A_{2A}$ receptor antagonistic activity, such as compounds (I) to (VII) and the like, or pharmaceutically acceptable salts thereof are effective as therapeutic and/or preventive agents for migraine.

Test Example 5

Effect on Extravasation into the Dura Mater Induced by Electrostimulation of Anesthetized Rat Trigeminal Nerve SD rats (male, Charles River) were anesthetized by intraperitoneal administration of sodium pentobarbital (60 mg/kg; Tokyo Chemical Industry Co., Ltd.). The distal portion of the trigeminal nerve was detached, and fixed to a stimulation bipolar electrode (tungsten line, 5 mm in width). After 5 minutes from the intravenous administration of Evans Blue (10 w/v %, 30 mL/kg; Sigma), the trigeminal nerve was electrostimulated for 30 seconds in the same manner as in Test Example 3. After immediate transcardial perfusion with physiological saline for 5 minutes, the dura mater was removed, and weighed to find the wet weight. The Evans Blue in the dura mater was extracted with formamide (Wako Pure Chemical Industries, Ltd.) at 60° C. for 24 hours, and absorbance at 625 nm was measured using an absorption spectrometer (Model: Power Wave X; Bio-Tec-Instrument). The Evans Blue concentration in the extract was calculated from the standard curve created from a standard sample of Evans Blue, and compensated with the dura mater weight. The test compound or the solvent was given 30 minutes before the electrostimulation. Leakage of Evans Blue into the dura mater was compared between the test compound-administered group and the solvent-administered group.

It was demonstrated that the extravasation into the dura mater based on the activation of the trigeminal nerve can be suppressed in the test compound-administered group when the compound having a selective adenosine $A_{2A}$ receptor antagonistic activity of the present invention is used as the test compound.

It is considered from the test result that the compounds having a selective adenosine $A_{2A}$ receptor antagonistic activity, such as compounds (I) to (VII) and the like, or pharmaceutically acceptable salts thereof are effective as therapeutic and/or preventive agents for migraine.

Test Example 6

Effect on Cortical Spreading Depression in Anesthetized Rat

The test was performed using the secondary cerebral blood flow repeated increase by cortical spreading depression [*NeuroReport*, Vol. 17, p. 1709 (2006)] as an index. There is a report that migraine preventive drugs have suppressing effects for cortical spreading depression [*Annals of Neurology*, Vol. 59, p. 652 (2006)].

SD rats (male, Charles River) were anesthetized by intraperitoneal administration of sodium pentobarbital (60 mg/kg; Tokyo Chemical Industry Co., Ltd.). The cervical region was cut open, and a tracheal catheter was inserted. A blood-pressure measuring catheter was inserted to the right femoral artery. The rat was fixed to a stereotaxic instrument (stereotaxic instrument for rats; Summit Medical), and the body temperature was maintained at 37° C. on a body temperature-maintaining heating pad (Model: CMA/150; Carnegie Medicine). Two cranial windows, each with a diameter of about 5 mm, were formed over the cerebral cortex (a cranial window for measuring cerebral blood flow; AP: −1.5, L: −1, H: −1.5, and a cranial window used to add a potassium chloride solution; AP: −4.5, L: −1, H: −4.5). A Laser Doppler Flowmeter (Model: ALF-2100; Advance) was used for the measurement of cerebral blood flow. Mean blood pressure was recorded on a pen-type recorder (Model: Type 3066; Yokogawa Electric Corporation) through measurement from a pressure transducer (Model: DX-312; Nihon Kohden Corporation) via a strain pressure amplifier (Model: AP-612GA; Nihon Kohden Corporation), using a polygraph system (Model: RM6000; Nihon Kohden Corporation). Arterial blood gas partial pressure (pH, $PaO_2$, $PaCO_2$) was measured using a laptop hemanalysis system (Model: AVL-OPTI-CCA; Sysmex).

After the addition of a potassium chloride solution (2 mol/L, 0.01 mL) through the cranial window, changes in cerebral blood flow over a 30-min time period were measured to evaluate cortical spreading depression. The test compound or the solvent was administered 30 minutes before the addition of potassium chloride. The influence on cerebral blood flow-repeated increase was compared between the test compound-administered group and the solvent group.

It was demonstrated that the cerebral blood flow-repeated increase can be suppressed in the test compound-administered group when the compound having a selective adenosine $A_{2A}$ receptor antagonistic activity or a pharmaceutically acceptable salt thereof of the present invention is used as the test compound.

It is considered from the test result that the compounds having a selective adenosine $A_{2A}$ receptor antagonistic activity, such as compounds (I) to (VII) or the like, or pharmaceutically acceptable salts thereof are effective as preventive agents for migraine.

It is also considered from the test result that drug resistance does not develop by the repeated administration of the compounds having a selective adenosine $A_{2A}$ receptor antagonistic activity, such as compounds (I) to (VII) or the like, or pharmaceutically acceptable salts thereof.

The compound having a selective adenosine $A_{2A}$ receptor antagonistic activity or a pharmaceutically acceptable salt thereof of the present invention can be administered alone. However, usually, the compound having a selective adenosine $A_{2A}$ receptor antagonistic activity or a pharmaceutically acceptable salt thereof of the present invention is preferably provided in various pharmaceutical preparations. Such pharmaceutical preparations can be used for animals and humans.

The pharmaceutical preparation according to the present invention may contain as the active ingredient a compound having a selective adenosine $A_{2A}$ receptor antagonistic activity or a pharmaceutically acceptable salt thereof either alone or as a mixture with any other therapeutic active ingredient. Furthermore, these pharmaceutical preparations are prepared by mixing the active ingredient with one or more pharmaceutically acceptable carriers (for example, diluents, solvents, excipients, or the like), and then subjecting the mixture to any method well-known in the technical field of pharmaceutics.

As for the administration route, it is preferred to select the most effective route of administration for treatment. Examples of the administration route include oral administration, and parenteral administration, for example, such as intravenous, nasal, and inhalation administration.

Examples of dosage form include tablets, injections, nasal preparations, inhalations, and the like.

Suitable dosage forms for the oral administration, for example, tablets, can be prepared by using excipients such as lactose, disintegrators such as starch, lubricants such as magnesium stearate, or binders such as hydroxypropylcellulose, or the like.

Suitable dosage forms for the parenteral administration, for example, injections, can be prepared by using diluents or solvents such as a saline solution, a glucose solution, or a mixture of brine and glucose solution, or the like.

The nasal preparation can be prepared as a solution preparation, for example, by adding the active ingredient to sterile purified water with optional component(s) including, for example, tonicity agents such as sodium chloride, antiseptics such as a p-hydroxybenzoic acid ester, buffer agents such as a phosphate buffer, or the like. Alternatively, the nasal preparation can be prepared as a suspension preparation by mixing the active ingredient with dispersant (s) such as polyethylene glycol 400, or the like, or as a powder preparation by mixing the active ingredient with carrier(s) such as hydroxypropylcellulose with optional component(s) including, for example, mucosa adherent base(s) such as Carbopol, or the like.

The inhalations can be prepared by blending the active ingredient, either in a powder or liquid form, into inhalation aerosol(s) or carrier(s), and by charging the mixture into inhaler(s), for example, such as metered dose inhaler(s), nebulizer(s), or dry powder inhaler(s). A wide range of conventionally known inhalation aerosols can be used, including, for example, a chlorofluorocarbon gas such as CFC-11; an alternative CFC gas such as HFA-227; a hydrocarbon gas such as propane, isobutane, and n-butane; diethyl ether; a nitrogen gas; a carbon dioxide gas, and the like. A wide range of conventionally known carriers can be used, including, for example, sugars, sugar alcohols, amino acids, and the like. The preferred examples include lactose, D-mannitol, and the like.

The doses and the frequencies of administration of the compound having a selective adenosine $A_{2A}$ receptor antagonistic activity or a pharmaceutically acceptable salt thereof of the present invention may vary depending upon dosage form, age and body weight of a patient, nature or seriousness of the symptom to be treated, or the like. In the oral administration, in general, a dose of 0.001 to 1,000 mg, preferably, 0.05 to 100 mg, is administered to an adult patient once or several times a day. In the parenteral administration such as the intravenous administration, nasal administration, and inhalation, in general, a dose of 0.001 to 1,000 mg, preferably, 0.01 to 100 mg, is administered to an adult patient once or several times a day. However, these doses and frequencies of administration vary by the various conditions described above.

The present invention, including the therapeutic and/or preventive agents for migraine, and the methods for treating and/or preventing migraine, has superior therapeutic and/or preventive effect for headache such as migraine. Further, as described above, the compounds having a selective adenosine $A_{2A}$ receptor antagonistic activity, including, for example, compounds (I) to (VII) and the like, or pharmaceutically acceptable salts thereof may be used in combination with one or more other pharmaceutical components.

Examples of other pharmaceutical components used in combination include known medicaments useful as, for example, therapeutic and/or preventive agents for headache, for example, such as migraine (*Pharmacology & Therapeutics*, 2006, 112, p. 199-212). Specific examples include $5\text{-HT}_1$ agonists [for example, triptans such as almotriptan, eletriptan, frovatriptan, naratriptan, rizatriptan, sumatriptan, and zolmitriptan; $5\text{-HT}_{1D}$ agonists such as PNU-109291, and PNU-142633; $5\text{-HT}_{1F}$ agonists such as LY334370; and the like], γ-aminobutyric acid agonists [for example, such as valproate, and divalproex], dopamine antagonists [for example, such as droperidol, and loxapine], glutamate modulators [for example, non-selective α-amino-3-hydroxy-5-methyl-4-isoxazolepropionic acid (AMPA)/kainic acid (KA) antagonists (non-selective AMPA/KA antagonists) such as LY293558, and E2007; metabotropic glutamate receptor modulators such as ADX-10059; $NR_{2B}$ antagonists such as CP-101,606; glycine-site antagonists such as ZD9379; and the like], adenosine $A_1$ receptor agonists [for example, such as GR79236], calcitonin gene-related peptide (CGRP) antagonists [for example, such as BIBN4096BS, and MK-0974], nitric oxide (NO) synthase inhibitors [for example, such as $N^G$-methyl-L-arginine hydrochloride (546C88), and GW-274150], vanilloid receptor modulators [for example, such as capsaicin, civamide, and zucapsaicin], somatostatin receptor agonists, angiotensin modulators [for example, angiotensin II (AT)-1 receptor inhibitors such as candesartan; angiotensin-converting enzyme (ACE) inhibitors such as lisinopril; and the like], antidepressants [for example, such as amitriptyline, venlafaxine, mirtazapine, milnacipran, and duloxetine], antiepileptic drugs [for example, gabapentinoids such as gabapentin, and pregabalin; topiramate; Srx-502; zonisamide; locosamide; and the like], calcium channel blockers [for example, such as verapamil, flunarizine, lomerizine, and nimodipine], acetaminophens, isometheptanes, ergots [for example, such as ergotamine, and dihydroergotamine], non-steroidal anti-inflammatory drugs (NSAIDs) [for example, such as aspirin, diclofenac, flurbiprofen, ibuprofen, ketoprofen, mefenamic acid, naproxen, rofecoxib, tolfenamic acid, and nimesulide], adrenergic receptor modulators [for example, α2-adrenergic agonists such as clonidine, and tizanidine; β-adrenergic blockers such as atenolol, metoprolol, nadolol, propranolol, timolol; and the like], 5-$HT_2$ antagonists [for example, such as methysergide, and pizotifen], sigma receptor (σR1) agonists [for example, such as dextromethorphan, carbetapentane, and 4-IBP], K-current modulators, chloride channel enhancers [for example, such as BTS72664], connexin hemi-channel modulators [for example, such as fenamate NSAIDs], magnesium, riboflavin, co-enzyme Q10, botulinum toxin, tonaberast, steroidal anti-inflammatory drugs [for example, such as dexamethasone], acetylcholine receptor modulators [for example, such as donepezil], and the like.

The dosage form of the compound having a selective adenosine $A_{2A}$ receptor antagonistic activity, such as compounds (I) to (VII) or the like, or a pharmaceutically acceptable salt thereof, when used in combination with other pharmaceutical component(s) is not particularly limited, as long as (a) the compound having a selective adenosine $A_{2A}$ receptor antagonistic activity, such as compounds (I) to (VII) or the like, or a pharmaceutically acceptable salt thereof, and (b) other pharmaceutical component(s) are combined at the time of administration. For example, the components (a) and (b) may be used or administered as a single agent (combination agent) or as a combination of more than one preparation, provided that these agents are prepared to contain these components. When administered as a combination of more than one preparation, the preparations may be administered at the same time or separately with a time lag. Preferably, these preparations are used in the form of, for example, tablets, injections, nasal preparations, inhalations, or the like. Furthermore, these preparations are prepared using any method well-known in the technical field of pharmaceutics, as above.

When administered as a combination of more than one preparation, for example, (a) a first component that contains the compound having a selective adenosine $A_{2A}$ receptor antagonistic activity, such as compounds (I) to (VII) or the like, or a pharmaceutically acceptable salt thereof, and (b) a second component that contains other pharmaceutical component(s) may be separately prepared into a kit, and may be administered to the same subject in the same route or in different routes at the same time or with a time lag, using the kit.

The kit is provided in the form of two or more containers (for example, vials, bags, or the like) with contents, so that the first and second content components can be administered in different routes (for example, tubes, or the like) or in the same route. The material, shape, or other variables of the containers are not particularly limited, as long as, for example, the content components of the containers do not undergo changes in response to external temperature or light, or the chemical components do not dissolve out of the containers during the storage. Specifically, the kit may be for tablets, injections, nasal preparations, inhalations, or the like.

When the compound having a selective adenosine $A_{2A}$ receptor antagonistic activity, such as compounds (I) to (VII) or the like, or a pharmaceutically acceptable salt thereof, is used in combination with other pharmaceutical component(s), (a) the compound having a selective adenosine $A_{2A}$ receptor antagonistic activity, such as compounds (I) to (VII) or the like, or a pharmaceutically acceptable salt thereof, and (b) other pharmaceutical component(s) may be administered at the same time or separately with a time lag. The doses vary depending on combinations of different factors such as administration subject, administration route, disorder, and pharmaceutical component, and the like, and should be decided according to the doses used in the clinic.

For example, in the oral administration in the form of, for example, tablets, in general, (a) the compound having a selective adenosine $A_{2A}$ receptor antagonistic activity, such as compounds (I) to (VII) or the like, or a pharmaceutically acceptable salt thereof, and (b) other pharmaceutical component(s) are given in the doses of 0.001 to 1,000 mg and 0.01 to 3,000 mg, preferably 0.05 to 1,000 mg and 0.1 to 3,000 mg, further preferably 0.05 to 100 mg and 0.1 to 3,000 mg, even more preferably 0.5 to 100 mg and 0.1 to 3,000 mg, respectively, to an adult patient once or several times a day, either at the same time or separately with a time lag.

Further, for example, in the parenteral administration in the form of, for example, injections, in general, (a) the compound having a selective adenosine $A_{2A}$ receptor antagonistic activity, such as compounds (I) to (VII) or the like, or a pharmaceutically acceptable salt thereof, and (b) other pharmaceutical component(s) are given in the doses of 0.001 to 1,000 mg and 0.001 to 3,000 mg, preferably 0.001 to 500 mg and 0.01 to 3,000 mg, further preferably 0.01 to 300 mg and 0.01 to 3,000 mg, even more preferably 0.01 to 100 mg and 0.01 to 3,000 mg, respectively, to an adult patient once or several times a day, either at the same time or separately with a time lag.

The doses and the frequencies of administration of (a) the compound having a selective adenosine $A_{2A}$ receptor antagonistic activity such as compounds (I) to (VII) or the like, or a pharmaceutically acceptable salt thereof, and (b) other pharmaceutical component(s) are not limited to the foregoing examples, because the doses and the frequencies of administration are appropriately set depending upon effectiveness of the active ingredients, dosage form, age and body weight of a patient, symptom, and the like.

The following more specifically describes the present invention by way of Examples. It should be noted, however, that the scope of the present invention is not limited by the following Examples.

EXAMPLE 1

Tablet

Compound IB

Tablets having the following ingredients are prepared according to the conventional manner. Compound IB (40 g), lactose (286.8 g), and potato starch (60 g) are mixed, and then a 10% aqueous solution of hydroxypropylcellulose (120 g) is added thereto. The resulting mixture is kneaded according to the conventional manner, granulated, and dried to form granules for tableting. After adding thereto 1.2 g of magnesium stearate followed by mixing, the mixture is punched with a tableting machine having a punch measuring 8 mm in diameter (Model RT-15; Kikusui) to obtain tablets (containing 20 mg of an active ingredient per tablet).

TABLE 3

| Formulation | Compound IB | 20 mg |
| --- | --- | --- |
| | Lactose | 143.4 mg |
| | Potato starch | 30 mg |
| | Hydroxypropylcellulose | 6 mg |
| | Magnesium stearate | 0.6 mg |
| | | 200 mg |

EXAMPLE 2

Tablet

Compound IIC

Tablets having the following ingredients are prepared in the same manner as in Example 1.

TABLE 4

| Formulation | Compound IIC | 20 mg |
| --- | --- | --- |
| | Lactose | 143.4 mg |
| | Potato starch | 30 mg |
| | Hydroxypropylcellulose | 6 mg |
| | Magnesium stearate | 0.6 mg |
| | | 200 mg |

EXAMPLE 3

Tablet

Compound IIIA

Tablets having the following ingredients are prepared in the same manner as in Example 1.

TABLE 5

| Formulation | Compound IIIA | 20 mg |
| --- | --- | --- |
| | Lactose | 143.4 mg |
| | Potato starch | 30 mg |
| | Hydroxypropylcellulose | 6 mg |
| | Magnesium stearate | 0.6 mg |
| | | 200 mg |

EXAMPLE 4

Tablet

Compound VA

Tablets having the following ingredients are prepared in the same manner as in Example 1.

TABLE 6

| Formulation | Compound VA | 20 mg |
| --- | --- | --- |
| | Lactose | 143.4 mg |
| | Potato starch | 30 mg |
| | Hydroxypropylcellulose | 6 mg |
| | Magnesium stearate | 0.6 mg |
| | | 200 mg |

EXAMPLE 5

Injection

Compound IA

Injections having the following ingredients are prepared according to the conventional manner. Compound IA (1 g) is added to distilled water for injection followed by mixing. After adjusting the pH of the mixture to 7 by adding hydrochloric acid and a sodium hydroxide aqueous solution thereto, the total volume is adjusted to 1,000 mL with distilled water for injection. The resulting mixture is aseptically charged into glass vials in 2-mL portions to obtain injections (containing 2 mg of an active ingredient per vial).

TABLE 7

| Formulation | Compound IA | 2 mg |
| --- | --- | --- |
| | Hydrochloric acid | Appropriate amount |
| | Sodium hydroxide aqueous solution | Appropriate amount |
| | Distilled water for injection | Appropriate amount |
| | | 2.00 mL |

EXAMPLE 6

Injection

Compound IIA

Injections having the following ingredients are prepared in the same manner as in Example 5.

TABLE 8

| Formulation | Compound IIA | 2 mg |
| --- | --- | --- |
| | Hydrochloric acid | Appropriate amount |
| | Sodium hydroxide aqueous solution | Appropriate amount |
| | Distilled water for injection | Appropriate amount |
| | | 2.00 mL |

EXAMPLE 7

Injection

Compound IV

Injections having the following ingredients are prepared in the same manner as in Example 5.

TABLE 9

| Formulation | Compound IV | 2 mg |
| --- | --- | --- |
| | Hydrochloric acid | Appropriate amount |
| | Sodium hydroxide aqueous solution | Appropriate amount |
| | Distilled water for injection | Appropriate amount |
| | | 2.00 mL |

EXAMPLE 8

Injection

Compound VI

Injections having the following ingredients are prepared in the same manner as in Example 5.

TABLE 10

| Formulation | Compound VI | 2 mg |
|---|---|---|
| | Hydrochloric acid | Appropriate amount |
| | Sodium hydroxide aqueous solution | Appropriate amount |
| | Distilled water for injection | Appropriate amount |
| | | 2.00 mL |

EXAMPLE 9

Nasal Preparation

Compound IB

Nasal preparations having the following ingredients are prepared according to the conventional manner. Compound IB (10 mg) and sodium chloride (0.9 g) are added to about 80 mL of sterile purified water, and dissolved therein by thorough stirring. Then, sterile purified water is added thereto to make the total volume 100 mL and to obtain nasal preparations. The resulting mixture is charged into nasal containers in 1-mL portions to obtain nasal preparations (containing 0.1 mg of an active ingredient per container).

TABLE 11

| Formulation | Compound IB | 0.1 mg |
|---|---|---|
| | Sodium chloride | 9.0 mg |
| | Sterile purified water | Appropriate amount |
| | | 1.0 mL |

EXAMPLE 10

Nasal Preparation

Compound IIC

Nasal preparations having the following ingredients are prepared in the same manner as in Example 9.

TABLE 12

| Formulation | Compound IIC | 0.1 mg |
|---|---|---|
| | Sodium chloride | 9.0 mg |
| | Sterile purified water | Appropriate amount |
| | | 1.0 mL |

EXAMPLE 11

Nasal Preparation

Compound VII

Nasal preparations having the following ingredients are prepared according to the conventional manner. Hydroxypropylcellulose (49 g) and carboxymethylcellulose (49 g) are added to compound VII (2 g), and the mixture is thoroughly mixed. The resulting powder mixture is charged into nasal containers in 1-g portions to obtain nasal preparations (containing 0.1 g of an active ingredient per container).

TABLE 13

| Formulation | Compound VII | 0.02 g |
|---|---|---|
| | Hydroxypropylcellulose | 0.49 g |
| | Carboxymethylcellulose | 0.49 g |
| | | 1.00 g |

EXAMPLE 12

Dry Powder Inhalation

Compound IB

Compound IB (10 g) is pulverized under the air pressure of 5 kg/cm$^2$ at a feed rate of 1.5 g/min, using a jet mill (A-OJET; Seishin Enterprise Co., Ltd.) The pulverized compound (I) and lactose (Pharmatose 325M; DMV) are mixed at a weight ratio of 1:5 to obtain dry powder preparations.

TABLE 14

| Formulation | Compound (IB) | 16.7 mg |
|---|---|---|
| | Lactose | 83.3 mg |
| | | 100 mg |

INDUSTRIAL APPLICABILITY

The present invention can provide therapeutic and/or preventive agents for migraine which comprise, as an active ingredient, a compound having a selective adenosine $A_{2A}$ receptor antagonistic activity or a pharmaceutically acceptable salt thereof; therapeutic and/or preventive agents for migraine which comprise, as an active ingredient, a compound having a selective adenosine $A_{2A}$ receptor antagonistic activity, which has an affinity for the adenosine $A_{2A}$ receptor 10 times or higher than that for the adenosine $A_1$ receptor, or a pharmaceutically acceptable salt thereof; and the like.

The invention claimed is:

1. A method for treating migraine with aura, which comprises administering to a human patient suffering from migraine with aura an effective amount of a compound according to formula IIC

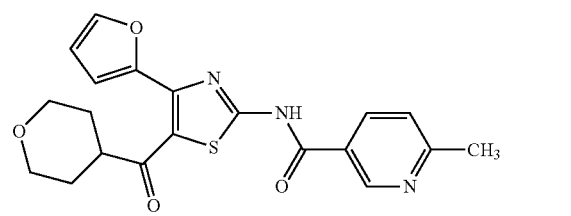

(IIC)

or a pharmaceutically acceptable salt thereof.

* * * * *